(12) United States Patent
Steele (10) Patent No.: US 8,784,420 B2
(45) Date of Patent: Jul. 22, 2014

(54) SURGICAL INSTRUMENTS FOR CUTTING ELONGATED ELEMENTS AND METHODS OF USE

(75) Inventor: Bradley Steele, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 793 days.

(21) Appl. No.: 12/903,785

(22) Filed: Oct. 13, 2010

(65) Prior Publication Data

US 2012/0095467 A1 Apr. 19, 2012

(51) Int. Cl.
*A61B 17/00* (2006.01)

(52) U.S. Cl.
USPC .......................................................... 606/79

(58) Field of Classification Search
USPC ........... 81/342, 383.5, 383, 395; 606/79, 157, 606/167, 174; 30/279.2
See application file for complete search history.

(56) References Cited

U.S. PATENT DOCUMENTS

| | | | |
|---|---|---|---|
| 657,203 A | 9/1900 | Neumeier, Jr. | |
| 1,592,017 A | 7/1926 | Van Campen | |
| 2,497,211 A | 2/1950 | Decarlo | |
| 3,636,954 A | 1/1972 | Weston | |
| 4,028,971 A | 6/1977 | Budrose | |
| 4,868,986 A * | 9/1989 | Olson et al. | 30/193 |
| 5,968,054 A * | 10/1999 | Yeatts et al. | 606/120 |
| 6,852,117 B2 | 2/2005 | Orlowski | |
| 7,444,907 B2 * | 11/2008 | Seber et al. | 81/367 |
| 7,497,867 B2 | 3/2009 | Lasner et al. | |
| 7,520,886 B2 | 4/2009 | Surti | |
| 7,574,805 B1 | 8/2009 | Lindroth | |
| 7,594,916 B2 | 9/2009 | Weinberg | |
| 7,645,291 B2 | 1/2010 | Ross et al. | |
| 2005/0080425 A1 | 4/2005 | Bhatnagar et al. | |
| 2005/0209624 A1 | 9/2005 | Vijay | |
| 2006/0052818 A1 | 3/2006 | Drake et al. | |
| 2008/0114367 A1 | 5/2008 | Meyer | |
| 2009/0222020 A1 | 9/2009 | Schmuck et al. | |
| 2009/0264887 A1 | 10/2009 | Beale et al. | |
| 2010/0114138 A1 | 5/2010 | Graham | |

FOREIGN PATENT DOCUMENTS

| | | |
|---|---|---|
| DE | 20002877 U1 | 4/2000 |
| FR | 2735350 A1 | 12/1996 |
| FR | 2929500 A1 | 10/2009 |

* cited by examiner

*Primary Examiner* — Anu Ramana (57) ABSTRACT

A surgical instrument for cutting an elongated element. The surgical instrument may have a compact size for use in-situ during a surgical procedure. The surgical instrument is also configured to provide the necessary mechanical advantage to cut the elongated element. The surgical instrument may include first and second arms that are pivotally connected together at a pivot. The arms include blades positioned at or towards distal ends of the arms that act together to cut the elongated element. A force mechanism is positioned between the arms to pivot the arms between an open orientation and a closed cutting orientation. The force mechanism may be positioned directly between the arms to reduce the overall size of the instrument.

19 Claims, 7 Drawing Sheets

SURGICAL INSTRUMENTS FOR CUTTING ELONGATED ELEMENTS AND METHODS OF USE

BACKGROUND

The present application is directed to a surgical instruments for cutting elongated elements and, more particularly, to surgical instruments with pivoting first and second arms and a force mechanism attached to the arms.

Various surgical procedures include the use of elongated elements. One example includes a bone anchor with a first end that is seated in a bone and an elongated shaft that extends outward from the bone. Another example includes a pin that attaches together bone segments, separate tissues, bone and tissue, etc. Still another example includes an elongated rod that extends along and is attached to one or more bones, such a vertebral rod that extends along the spine or a rod that extends along a broken femur.

It may be necessary for sections of the elongated elements to be removed during the surgical procedure. Specifically, the removal of these sections often occurs at the end of the surgical procedure to remove excess sections of the elongated elements that serve no purpose and should not remain in the patient. These sections may include the portion of the bone anchor or pin that extends outward beyond the bone or tissue to which it is attached, and an end of the elongated rod that extends beyond an injury location.

A surgical instrument is necessary for removing the excess sections of the elongated elements. The surgical instrument should be sized to be used in a surgical setting and work within a limited space. The cutting portion of the surgical instrument should be sized to be inserted into the patient for cutting the elongated element at the proper location along the length. The surgical instrument should be designed to apply the necessary force to cut the elongated elements.

The surgical instrument should also be designed for use in cutting elongated elements that are not positioned in a patient. By way of example, elongated rods and bone anchors may be sized and cut prior to insertion into the patient.

SUMMARY

The present application is directed to surgical instruments for cutting an elongated element. The surgical instrument may include first and second arms each with an elongated shape, a distal section, a proximal section, and a cutting element positioned at the distal section. The first arm may further include a first aperture that extends longitudinally through at least a portion of the distal section and includes an inlet and an outlet spaced away from the inlet. The distal section of the second arm may further include a pair of spaced apart walls that form a longitudinal channel. The distal section of the first arm may be positioned in the channel of the second arm and in an overlapping arrangement with the walls of the second arm. A pivot member may be positioned in the distal sections of the first and second arms at a point where the arms are in the overlapping arrangement. The pivot member may be fixedly attached to the first arm and movable relative to the second arm. The pivot member may include a second aperture that aligns with the first aperture. A passage may be formed by the first aperture in the first arm and the second aperture in the pivot member. The passage may extend through the pivot member to receive a portion of the elongated element. A force mechanism may be attached to the proximal sections of the first and second arms to pivot the first and second arms about the pivot member between an open orientation with the cutting elements spaced apart and a closed orientation with the cutting elements positioned in proximity to each other.

The surgical instrument may also include first and second arms each with an elongated shape, a distal end, a proximal end, and a cutting element positioned in proximity of the distal end. The first and second arms may be positioned in an overlapping arrangement. A pivot member may be positioned in closer proximity to the distal ends than the proximal ends. The pivot member may extend across each of the first and second arms and pivotally connect the arms together with the arms movable between an open orientation with the distal ends being spaced apart and a closed orientation with the distal ends being spaced together. A force mechanism may be attached in proximity to the proximal ends of the first and second arms. The force mechanism may include a first set of links positioned on a first lateral side of the first and second arms, and a second set of links positioned on an opposing second lateral side of the first and second arms. The force mechanism may also include an elongated threaded element positioned between the first and second arms and between the first and second sets of links. The elongated threaded element may include a threaded section that extends along a limited length of the element, a first unthreaded section that extends between the threaded section and a distal end of the element, and a second unthreaded section positioned on an opposing side of the threaded section from the first unthreaded section. The force mechanism may include a connector with a threaded aperture that is positioned over the threaded section, and a first attachment with the first set of links and a second attachment with the second sets of links.

Methods of using the surgical instrument to cut elongated elements are also disclosed. The methods may include inserting an end of the elongated element into an inlet in a first arm of the surgical instrument. The method may include moving the first arm along the elongated element with the elongated element moving within a passage within an interior of the first arm and through a pivot that pivotally attaches the first arm to a second arm. The method may include aligning a first cutting element on the first arm with the elongated element. The method may include applying a force with a force mechanism attached to the arms and pivoting the second arm about the first arm at the pivot and moving a second cutting element on the second arm towards the first cutting element on the first arm. The method may include cutting the elongated element with the first and second cutting elements. The method may also include maintaining a cut section of the elongated element within the passage.

The various aspects of the various embodiments may be used alone or in any combination, as is desired.

DETAILED DESCRIPTION

Figure 1:
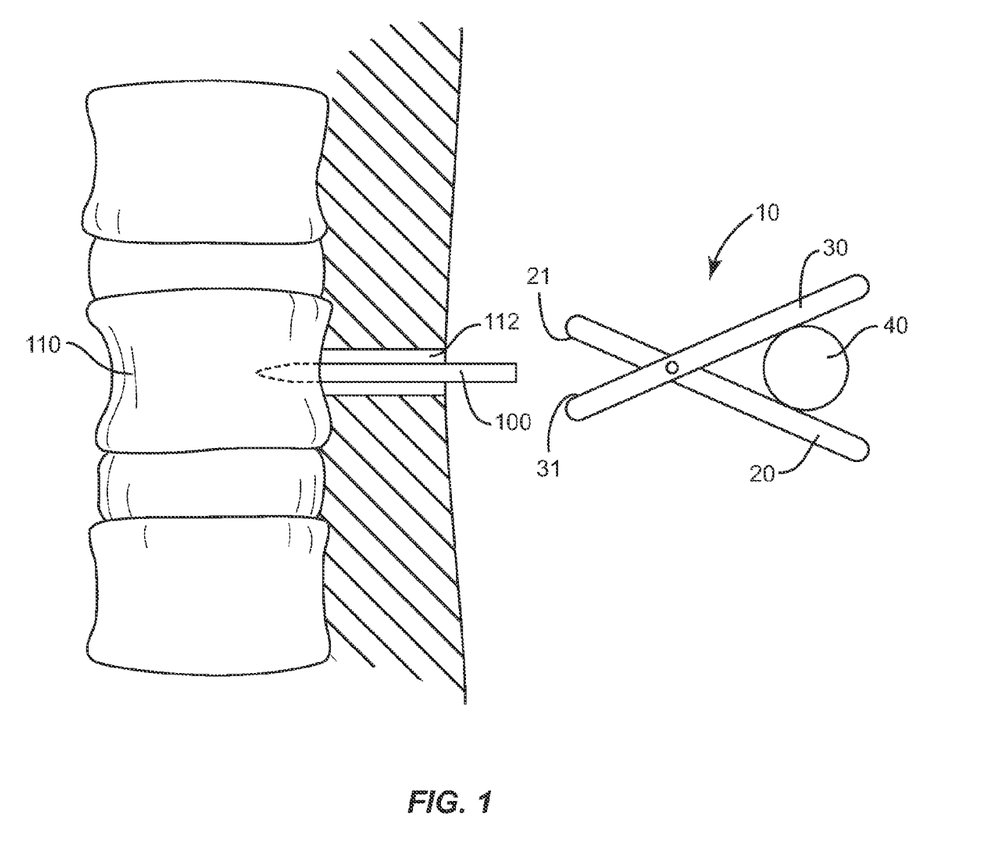
FIG. 1 is a schematic view of a surgical instrument and an elongated element in a surgical site.

The present application is directed to surgical instruments and methods of use for cutting an elongated element. The surgical instruments may have a compact size for use in-situ during a surgical procedure. The surgical instruments are also configured to provide the necessary mechanical advantage to cut the elongated element. FIG. 1 schematically illustrates a surgical instrument 10 that generally includes first and second arms 20, 30 that are pivotally connected together. The arms 20, 30 include blades 21, 31 positioned at or towards distal ends of the arms that act together to cut the elongated element 100. A force mechanism 40 is positioned between the arms 20, 30 to pivot the arms between an open orientation and a closed cutting orientation. The force mechanism 40 may be positioned directly between the arms 20, 30 to reduce the overall size of the instrument 10.

The instrument 10 is sized for use in a surgical setting with the cutting blades 21, 31 sized and positioned for insertion through an incision 112 and into a patient. The blades 21, 31 are positioned for cutting the elongated element 100 in close proximity to a bone 110 from which it extends. Further, the instrument 10 includes a length such that the force mechanism 40 may remain located outside of the patient during the cutting process.

Figure 2:
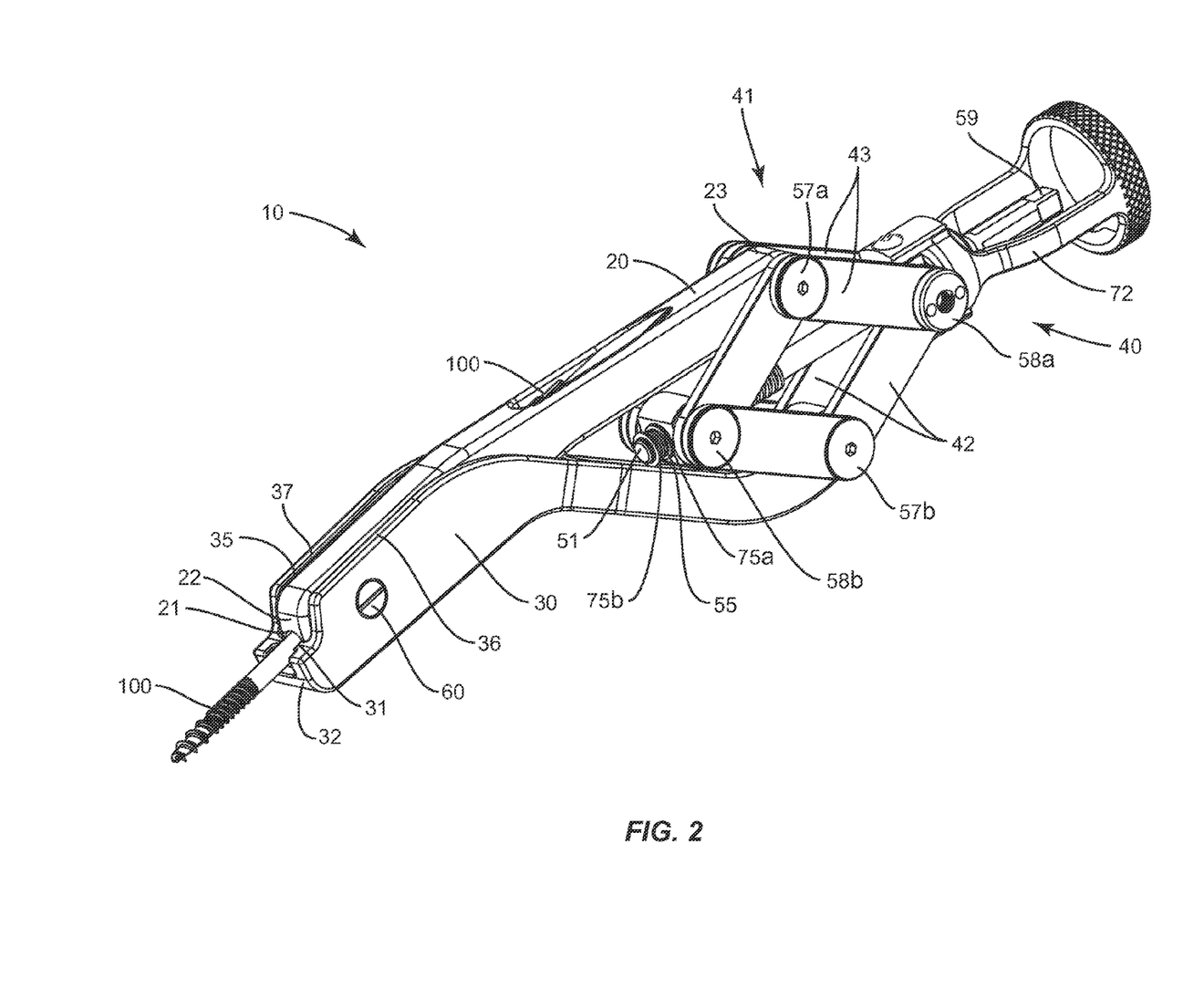
FIG. 2 is a perspective view of a surgical instrument and an elongated element.

FIG. 2 illustrates a perspective view of an instrument 10 with the force mechanism 40 attached to and located between the arms 20, 30. The shapes of the various elements and their relative positioning provides for an instrument 10 with a compact size that provides adequate force for cutting a variety of elongated elements 100.

Figure 3:
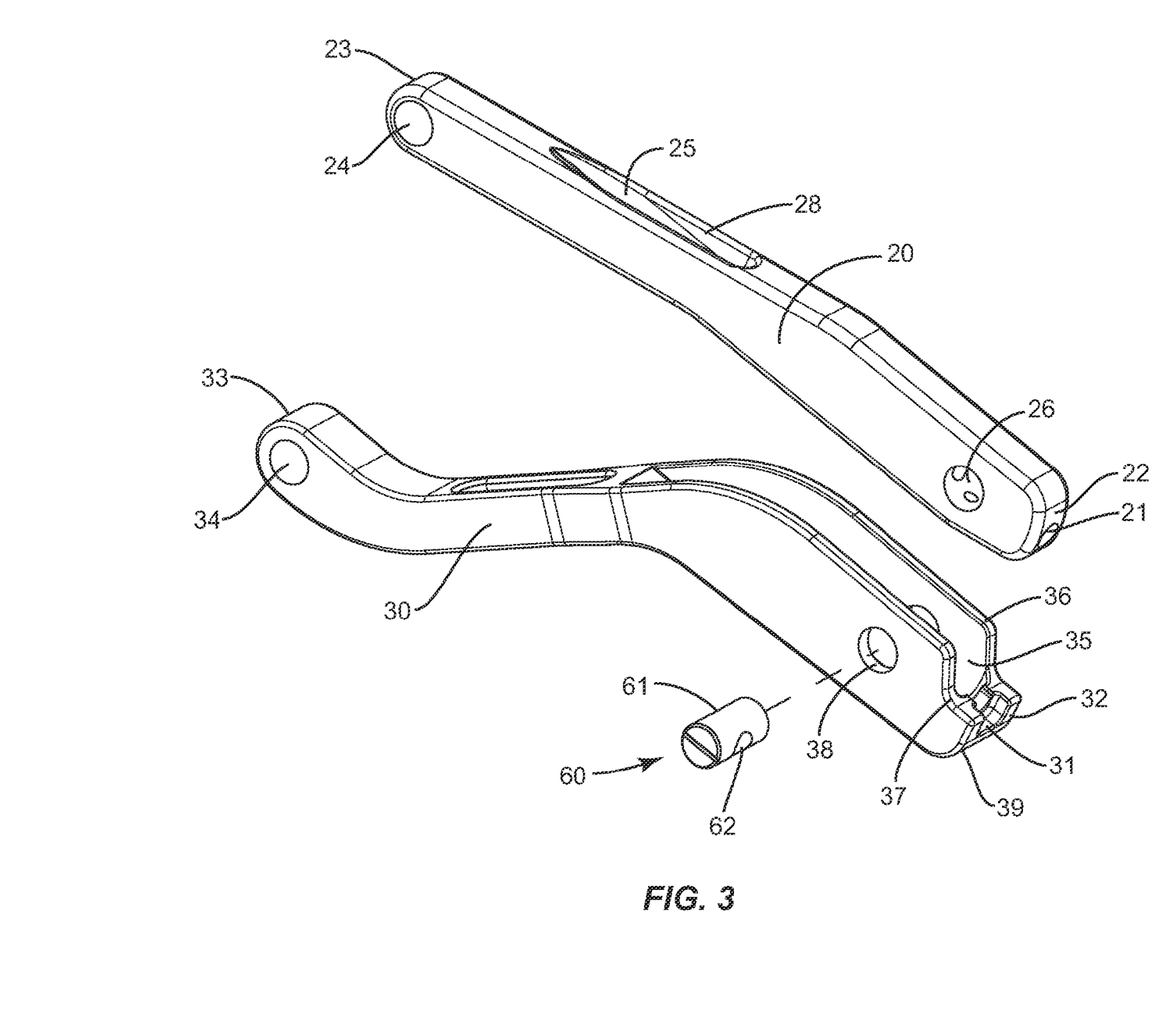
FIG. 3 is an exploded perspective view of first and second arms and a pivot member.

As illustrated in FIGS. 2 and 3, the first and second arms 20, 30 are pivotally connected together at a pivot 60. The blades 21, 31 are positioned at the distal ends 22, 32 of the respective arms 20, 30 and work together to form a cutting mechanism. The arms 20, 30 also include proximal ends 23, 33 respectively. The pivot 60 is positioned in closer proximity to distal ends 22, 32 than to the proximal ends 23, 33.

The first arm 20 includes a relative straight shape with a longitudinal axis being substantially straight and extending longitudinally through the distal end 22 and the proximal end 23. An aperture 24 is positioned at or in proximity to the proximal end 23 to attach to the force mechanism 40. Another aperture 26 is positioned towards the distal end 22 to form a part of the pivot 60 for pivotally attaching to the second arm 30. Each of the apertures 24, 26 extend across the longitudinal axis of the first arm 20.

Figure 7:
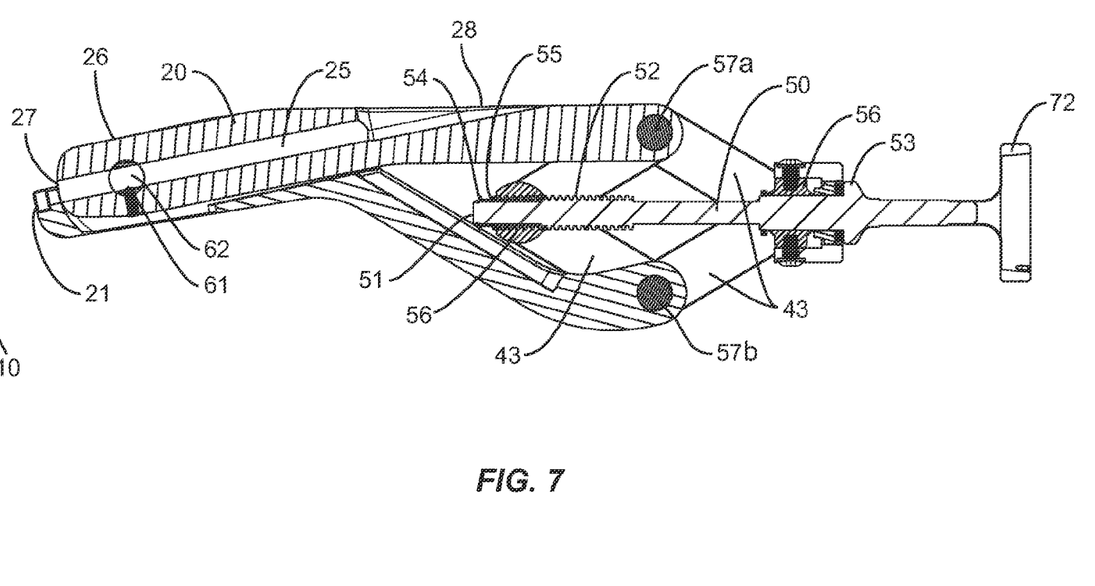
FIG. 7 is a sectional view cut along line VII-VII of FIG. 6.

As illustrated in FIGS. 3 and 7, a third aperture 25 extends longitudinally within an interior of the arm 20. The third aperture 25 includes a first end 27 at the distal end 22 and includes a second end 28 towards the proximal end 23. The third aperture 25 is designed to receive a portion of the elongated element 100 that is removed during the cutting process. As such, the third aperture 25 is sized and shaped to receive an end of the elongated element 100 and to move along the length of the elongated element to position the blades 21, 31 at the desired location along the length of the elongated element 100. Therefore, the third aperture 25 includes a larger cross-sectional size than the elongated element 100 to allow for this positioning. The third aperture 25 further extends through the pivot 60. The aperture 25 is positioned for the instrument 10 to cut an elongated element 100 of any length. The aperture 25 does not intersect the force mechanism 40 or the arms 20, 30 in a manner to block the elongated element 100. The instrument 10 thus may be moved along the elongated element 100 any distance.

The first arm 20 may be solid with the aperture 25 extending through an interior of the arm 20 as illustrated in FIG. 7. The first arm 20 may also have a cross-sectional shape that forms a "U" with an open central section and a pair of opposing sidewalls. The aperture 25 extends through the open central section between the sidewalls.

The second arm 30 includes a more non-linear shape than the first arm 20. The second end 30 extends between the distal end 32 and the opposing proximal end 33. The second arm 30 is curved at a point between the ends 32, 33 to position the proximal end 33 away from the proximal end 23 of the first arm 20. A longitudinal channel 35 is positioned at or in proximity to the distal end 32 to receive the first arm 20. FIGS. 2 and 3 illustrate the channel 35 starting in proximity to the distal end 32 and extending through the pivot aperture 26 and towards the proximal end 33. The channel 35 is formed between a pair of opposing side walls 36, 37 and a back wall 39. The channel 35 includes a width measured across a longitudinal axis of the second arm 30 and between the side walls 36, 37 that is equal to or larger than a width of the first arm 20 such that the arms 20, 30 are positioned in an overlapping configuration as illustrated in FIG. 2.

The second arm 30 also includes an aperture 34 at or in proximity to the proximal end 33 to attach to the force mechanism 40. Another aperture 38 extends across the second arm 30 to receive the pivot member 61. As illustrated in FIG. 3, aperture 38 may be formed by a pair of spaced-apart apertures positioned in the side walls 36, 37 of the second arm 30. Each of the apertures 34, 38 extend across a longitudinal axis of the second arm 30.

The pivot 60 includes a post 61 that attaches the arms 20, 30 together in an overlapping configuration. As illustrated in FIG. 3, the pivot 60 includes a post 61 that fits within the apertures 26, 38 in the first and second arms 20, 30. The post 61 may be fixedly attached to the first arm 20 and movable relative to the second arm 30. The attachment may be formed by one or more of soldering, adhesive, and mechanical fastener. In one embodiment, a pin extends through an aperture in the first arm 20 that extends into the aperture 26 and aligns with a cavity in the post 61. The post 61 may include a circular cross-sectional shape that matches the shape of the aperture 38 to facilitate pivoting movement of the second arm 30 about the post 61.

The post 61 includes an elongated shape with a central aperture 62. The aperture 62 extends through a width of the post 62 and across a longitudinal axis of the post 62. The aperture 62 includes a cross-sectional size to receive the elongated element 100. As illustrated in FIG. 7, the size of the aperture 62 is comparably to that of the aperture 25. The aperture 62 remains aligned with the aperture 25 in the first arm 20 as illustrated in FIG. 7. This alignment between the apertures 62, 25 is possible because the post 61 is fixed relative to the first arm 20. This allows for the elongated element 100 to be inserted into and extend through the apertures 62, 25 during the cutting process.

Figure 6:
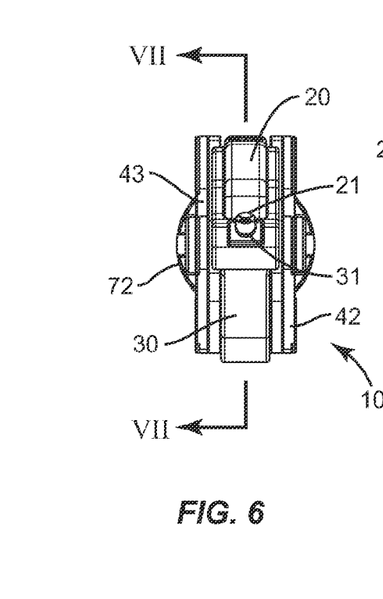
FIG. 6 is an end view of a surgical instrument according to one embodiment.

The blades 21, 31 are configured to work in combination to cut the elongated element 100. The blades 21, 31 may each include a sharpened surface that cut into the elongated element 100 during the cutting process. Alternatively, just one of the blades 21, 31 may be sharpened with the opposing blade providing a base for positioning and holding the element 100. One or both blades 21, 31 may be straight, or may have a rounded shape as best illustrated in FIG. 6. The radius of the rounded blades may roughly match the diameter of the elongated elements 100 that are to be cut.

The first and second arms 20, 30 are aligned to position the blade 21 of the first arm 20 directly in front of or directly behind the blade 31 of the second arm 30. FIG. 2 includes the blade 21 of the first arm 20 directly behind the blade 31 of the second arm 30. This positioning provides for the blades 21, 31 to move past one another to create a shearing effect to cut the elongated element 100.

The force mechanism 40 is attached to the arms 20, 30 and provides a force for pivoting the arms between cutting and non-cutting orientations. The force mechanism 40 generally includes linkages 41 and a threaded element 50. The force mechanism 40 may form a scissor-jack mechanism that provides a mechanical advantage for moving the arms 20, 30. The length of the arms 20, 30 locates the force mechanism 40 away from the pivot 60 to further provide for a mechanical advantage in pivoting the arms 20, 30.

The linkages 41 include first and second sets of links 42, 43. The first link set 42 is attached to a first lateral side of the arms 20, 30, and the second link set 43 is attached to an opposing second lateral side of the arms 20, 30. Each link set 42, 43 includes four separate links positioned with the ends in an overlapping arrangement. Each separate link includes apertures at or in proximity to the ends. A first fastener 57a extends through a pair of links in the first link set 42, through the aperture 24 in the arm 20, and through a pair of links in the second link set 43. A second fastener 57b extends through a different pair of links in the first link set 42, through the aperture 34 in the arm 30, and through a different pair of links in the second link set 43. Separate fasteners 58a, 58b further connect links of each of the sets 42, 43.

Figure 5A:
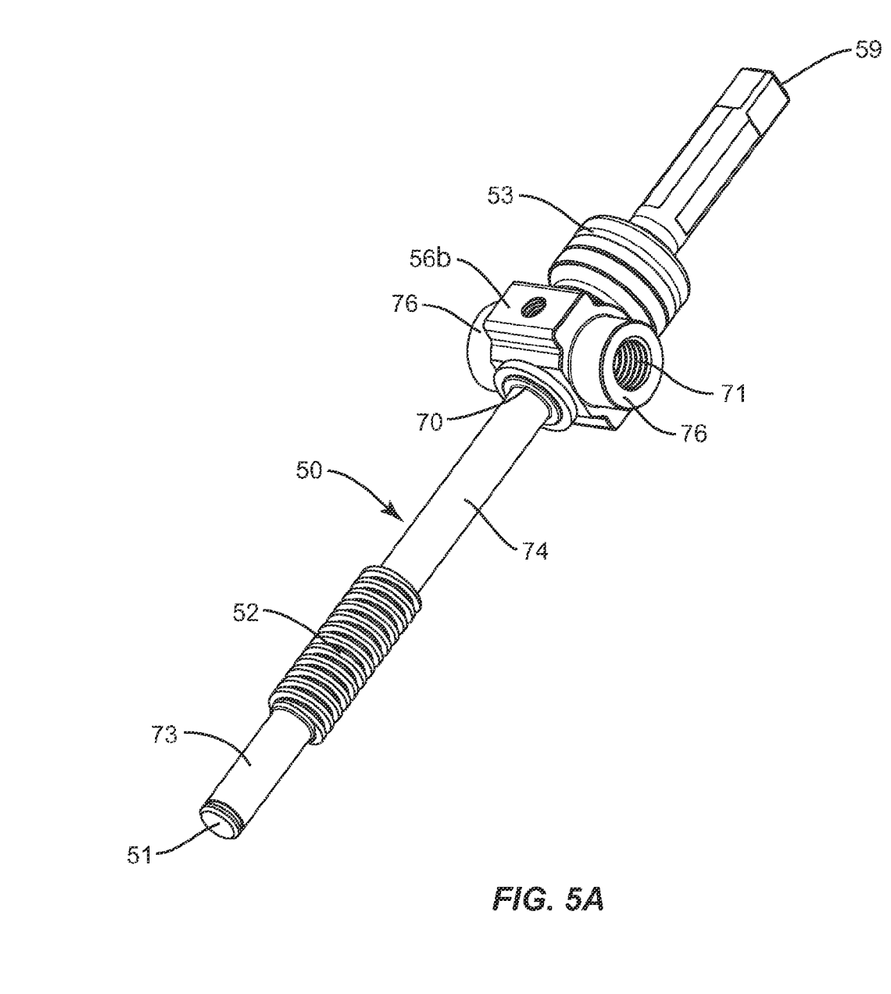
FIG. 5A is a perspective view of a threaded element and a second connector.
Figure 5B:
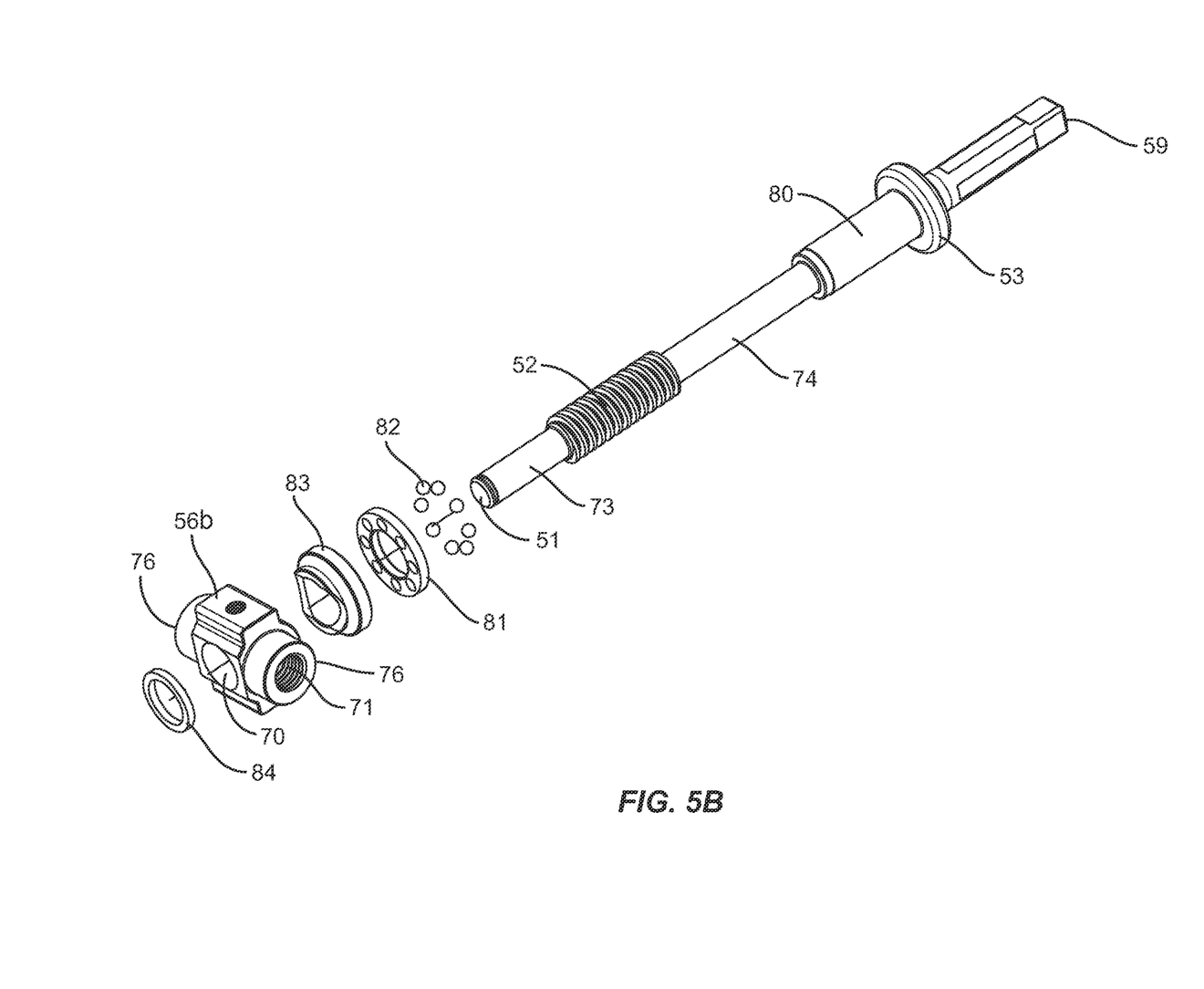
FIG. 5B is an exploded perspective view of a threaded element and a second connector.

The threaded element 50 is positioned between the first and second sets of links 42, 43. As best illustrated in FIGS. 5A and 5B, the threaded element 50 includes an elongated shape with a distal end 51 and a proximal end 59. A threaded section 52 extends along a limited length of the threaded element 50 in proximity to but spaced away from the distal end 51. A first non-threaded section 73 is positioned between the threaded section 52 and the distal end 51. A second non-threaded section 74 is positioned on an opposing side of the threaded section 52 (i.e., a proximal side of the threaded section 52). A third non-threaded section 80 is positioned on a proximal side of the second non-threaded section 74. The third non-threaded section 80 includes a larger cross-sectional size than the second non-threaded section 74. A flange 53 with a larger cross-sectional size than the third non-threaded section 80 is positioned at a proximal side of the third non-threaded section 80. A washer 81 is positioned over the third non-threaded section 80 and is separated from the flange 53 by bearings 82. A fixture 83 is positioned on a proximal side of a second connector 56b and a washer 84 is positioned on a distal side. Each of the washer 81, fixture 83, second connector 56b, and washer 84 include apertures sized to be loaded onto the threaded element 50 from the distal end 51 and moved axially into position along the third non-threaded section 80. The apertures are larger than the first and second non-threaded sections 73, 74, and the threaded section 52, and smaller than the flange 53.

A first connector 56a is positioned along the first non-threaded section 73. The first connector 56a includes an aperture 70 sized to receive the non-threaded section 73. The aperture 70 is larger than the first non-threaded section 73 for the first connector 56a to move axially along this section 73. The aperture 70 further includes threads that engage with the threaded section 52 for the first connector 56a to axially move along the threaded section 52 during rotation of the threaded element 50. The first connector 56a also includes a pair of opposing receptacles 71. The first receptacle 71 is sized to receive a first portion of the first fastener 58b to attach with the ends of two links of the first link set 42. The second receptacle 71 is sized to receive a second portion of the first fastener 58b to attach with the ends of two links of the second link set 43.

The receptacles 71 are positioned in extensions 76 that extend laterally outward from the first connector 56a. The extensions 76 include cross-sectional shapes and sizes to receive the apertures in the ends of the links. FIG. 5A includes the extensions 76 having a circular cross-sectional shape. The fastener 58 is then sized to maintain the links positioned on the extensions 76.

Figure 4:
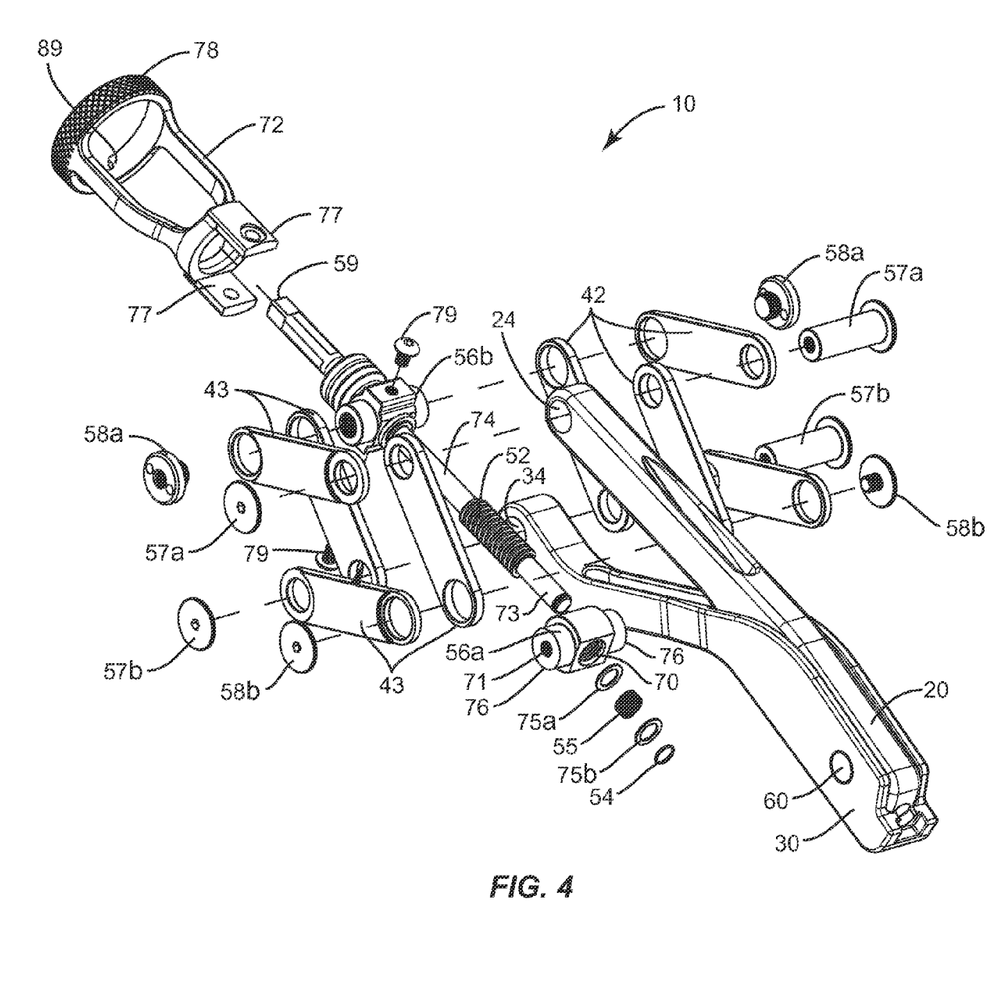
FIG. 4 is a partial exploded perspective view of a surgical instrument with first and second arms in an overlapping arrangement.

A biasing member 55 is attached to the threaded element 50 and acts on the first connector 56a to bias the first connector 56a towards the threaded section 52. The biasing member 55 may include a compression coil spring that extends around the threaded element 50. As illustrated in FIGS. 2 and 4, the biasing member 55 may also be associated with a pair of washers 75a, 75b that extend over the first non-threaded section 73 of the threaded element 50. The first washer 75a is positioned on a first axial side of the biasing element 55, and the second washer 75b is positioned on an opposing second axial side. The first washer 75a includes a larger cross-sectional size than the aperture 70 to prevent the first washer 75a and the biasing element 55 from moving into the first connector 56a.

The biasing member 55 is maintained on the threaded element 50 by a cap 54 attached at or in proximity to the distal end 51. The cap 54 includes a larger cross-sectional size than the second washer 75b to limit the extent of axial movement of the biasing member 55 along the threaded element 50. In one embodiment, the cap 54 is a c-shaped lock ring that fits into a groove formed at or in proximity to the distal end 51 of the threaded element 50.

The biasing member 55 further applies a force to the first connector 56a when it moves beyond the threaded section 52 and onto the first non-threaded section 73. The biasing member 55 biases the first connector 56a against the threaded section 52 to re-engage with the threaded section 52 upon an initial amount of rotation of the threaded element 50. Without the biasing member 55, the first connector 56a would not re-engage with the threaded section 52.

The second connector 56b is positioned along the third non-threaded section 80. The second connector 56b includes an aperture 70 sized to receive the third non-threaded section 80 of the threaded element 50. The second connector 56b may be axially fixed to the threaded element 50 and allow the threaded element 50 to rotate within the aperture 70. The second connector 56b also includes a pair of opposing receptacles 71 positioned in lateral extensions 76. The first receptacle 71 is sized to receive a first portion of the fasteners 58a to attach with the ends of two links of the first link set 42. The second receptacle 71 is sized to receive a second portion of the fasteners 58b to attach with the ends of two links of the second link set 43. The extensions 76 further include a cross-sectional shape sized to fit within the apertures in the links.

The proximal end 59 of the threaded element 50 extends proximally outward from the force mechanism 40. The proximal end 59 is configured to receive an exterior force for rotating the threaded element 50. FIGS. 4 and 5 include the proximal end 59 having a polygonal cross-sectional shape to engage with an exterior instrument for receiving the force. A variety of exterior instruments may be used, such as a POWEREASE™ Tapper-Driver from Medtronic, Inc., Minneapolis, Minn., a wrench, socket, screw driver, and power drill.

The proximal end 59 may also include a grip (not illustrated) for a medical practitioner to grasp and twist to rotate the threaded element 50.

An adapter 72 may be attached to the threaded element 50. The adapter 72 includes a grip 78 that is grasped and manipulated by a medical practitioner during the surgical procedure. The adapter 72 extends over the proximal end 59 such that the proximal end 59 is exposed for receiving an exterior force for rotating the threaded element 50. As illustrated in FIG. 4, the adapter 72 may include flanges 77 sized to engage with the second connector 56. Fasteners 79 extend through the flanges 77 and into the connector 56 for attaching the adapter 72 to the instrument 10. A cut-out 89 may be positioned along the adapter 72 to connect to a structural element to apply a counter-torque to the instrument 10 when an external rotational force is applied to the threaded element 59.

FIG. 6 is an end view of the instrument 10 viewed from the distal end. The force mechanism 40 is sized to fit between the arms 20, 30 giving the instrument 10 a reduced overall size. This facilitates use within a surgical setting when there is a minimum of available space.

In use, the instrument 10 is manipulated by the surgical practitioner and that arms 20, 30 are pivoted to the open orientation. The distal ends 22, 32 of the arms 20, 30 are inserted into the surgical site. The first end 27 of the aperture 25 in the first arm 20 is aligned with an end of the elongated element 100. The end of the elongated element 100 is inserted into the first end 27. The instrument 10 is moved further along the elongated element 100 with the end of the elongated element passing along the aperture 25. The end of the elongated element 100 may move beyond the second end of the aperture 25 and extend outward beyond the first arm 20.

Movement of the elongated element 100 along the aperture 25 in the first arm 20 includes the elongated element 100 through the pivot 60. The elongated element 100 is moved through the aperture 62 in the post 61 of the pivot 60.

The instrument 10 is further manipulated and the blades 21, 31 are positioned at the desired cut location on the elongated element 100. Once at the desired position, the instrument 10 is moved to the closed orientation.

Moving the instrument to the closed orientation includes applying a rotational force to the proximal end 59 of the threaded element 50. The force may be applied by an external tool that is attached to the proximal end 59, or by a medical practitioner grasping and applying the force by hand.

In the open orientation, the first connector 56 is towards the distal portion of the threaded section 52 of the threaded element 50. The biasing member 55 maintains the first connector 56 at least against the threaded section 52 and prevents the first connector 56 from moving axially outward beyond the threaded section 52 to prevent engagement. Rotation of the threaded element 50 causes the first connector 56 to engage with an axially move along the threaded section 52. The first connector 56 moves proximally along the threaded section 52 towards the second connector 56 that is axially fixed to the threaded element 50. This movement causes an increase in the height of the link sets 42, 43. This then causes the arms 20, 30 that are attached to the link sets 42, 43 to move apart and to move about the pivot 60 and to move the blades 21, 31 together.

Continued rotation of the threaded element 50 moves the instrument 10 to the closed orientation with the blades 21, 31 together to cut the elongated element 100. The cut section of the elongated element 100 is positioned in the aperture 25 in the first arm 20. This prevents the cut section from inadvertently falling into the patient or other undesirable location. The instrument 10 may be removed from the patient with the cut section remaining in the first arm 20. Once removed from the patient, the instrument 10 may be manipulated to remove the cut section.

The instrument 10 may be returned to the open orientation by rotating the threaded element 50 in the opposite direction. The first connector 56 axially moves along the threaded section 52. In the event the first connector 56 moves to the distal end of the threaded section 52, the biasing member 55 maintains the first connector 56 against the threaded section 52 such that rotation of the threaded member 50 to close the instrument 10 immediately re-engages the first connector 56 and the threaded section 52.

The instrument 10 is configured to cut a variety of different elongated elements 100. FIG. 1 includes the elongated element being a bone anchor with a length that extends outward from the bone 110. This example includes the elongated element 100 extending substantially perpendicularly outward from the bone 110, although other examples may include the elongated element 100 extending outward at different angular orientations. The elongated element 100 may also include pins, rods, and various like elements.

FIG. 1 further illustrates the instrument 10 used for during a vertebral surgical operation. The instrument 10 may also be used in various other surgical settings. Further, the instrument 10 may be used for cutting elongated elements 100 that are not attached to a patient and elongated elements 100 that are not within a patient.

Each set of links 42, 43 may include a total of four links including two pairs of upper and lower links as illustrated. One or both sets of links 42, 43 may also include a total of two links that include a single pair of links with one upper link and one lower link.

The instrument 10 may also include a single set of links. The single set may include a total of four links, or may include a total of just two links.

The instrument 10 may include various types of force mechanisms 40. The illustrated instrument 10 includes linkages 41 and a threaded element 50. Other force mechanisms 40 may be used for controlling the position of the arms 20, 30 and the pivoting movement between the open and closed orientations. One embodiment includes an inflatable member positioned between the arms 20, 30 that is inflated and deflated accordingly to adjust the orientation of the arms 20, 30. In one embodiment, the force mechanism 40 does not include links 41, but rather includes the first and second connectors 56a, 56b directly attached to the apertures 24, 34 in the arms 20, 30. Another embodiment includes a rack-and-pinion mechanism.

The instrument 10 may be used during surgical procedures on living patients. The instrument 10 may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical instrument for cutting an elongated element comprising:
    first and second arms each with an elongated shape, a distal section, a proximal section, and a cutting element positioned at the distal section;
    the first arm further including a pair of opposing sidewalls comprising a first aperture that extends longitudinally through at least a portion of the distal section of the pair of opposing sidewalls and includes an inlet and an outlet spaced away from the inlet;
    the distal section of the second arm further including a pair of spaced apart walls that form a longitudinal channel;
    the distal section of the first arm being positioned in the channel of the second arm and in an overlapping arrangement with the walls of the second arm;
    a pivot member positioned in a distal channel running transverse to the longitudinal channel through the distal sections of the first and second arms where the arms are in the overlapping arrangement, the pivot member being fixedly attached to the first arm and movable relative to the second arm, the pivot member including a second aperture that aligns with the first aperture;
    a passage formed by the first aperture in the first arm and the second aperture in the pivot member, the passage extending through the pivot member to receive a portion of the elongated element, wherein an inlet of the passage is at a distal end of the first arm and an outlet is on a top side of the first arm that faces away from the second arm, the outlet positioned along the first arm on an opposite side of the pivot member from the inlet; and
    a force mechanism attached to the proximal sections of the first and second arms to pivot the first and second arms about the pivot member between an open orientation with the cutting elements spaced apart and a closed orientation with the cutting elements positioned in proximity to each other.

2. The surgical instrument of claim 1, wherein the first arm is seated in the channel of the second arm and the cutting element of the first arm is positioned closer to the pivot member than the cutting element of the second arm with the cutting element of the first arm positioned behind the cutting element of the second arm when the first and second arms are in the closed orientation.

3. The surgical instrument of claim 1, wherein the pivot member has a cylindrical shape with a first end positioned in a first one of the walls of the second arm and a second end positioned in a second one of the walls and the second aperture extending through the pivot member between the first and second ends.

4. The surgical instrument of claim 1, wherein a distal end of the first arm is positioned inward from a distal end of the second arm.

5. The surgical instrument of claim 1, wherein the passage is straight and an axis of the pivot member is perpendicular to an axis of the passage.

6. The surgical instrument of claim 1, wherein the force mechanism includes a rotatable element to adjust the force mechanism, the rotatable element including an elongated shape that is parallel with the first aperture.

7. A method of cutting an elongated element attached to a patient with a surgical instrument comprising:
    providing a surgical instrument as described in claim 1;
    inserting an end of the elongated element into an inlet in a first arm of the surgical instrument;
    moving the first arm along the elongated element with the elongated element moving within a passage within an interior of the first arm and through a pivot that pivotally attaches the first arm to a second arm;
    aligning a first cutting element on the first arm with the elongated element;
    applying a force with a force mechanism attached to the arms and pivoting the second arm about the first arm at the pivot and moving a second cutting element on the second arm towards the first cutting element on the first arm;
    cutting the elongated element with the first and second cutting elements; and
    maintaining a cut section of the elongated element within the passage.

8. The method of claim 7, further comprising moving the first arm along the elongated element with the end of the elongated element moving through an outlet of the passage, the outlet positioned on an opposite side of the pivot from the inlet.

9. The method of claim 7, further comprising cutting the elongated element and moving the second cutting element in a row with the first cutting element along a longitudinal axis of the instrument.

10. The method of claim 7, further comprising pivoting the first arm relative to the second arm and moving the first arm in a channel formed between side walls in the second arm.

11. The method of claim 7, further comprising biasing a connector on a threaded element of the force mechanism to maintain the connector in contact with a threaded section of the threaded element.

12. A surgical instrument for cutting an elongated element comprising:
    first and second arms each with an elongated shape, a distal end, a proximal end, and a cutting element positioned in proximity of the distal end, the first arm positioned within the second arm in an overlapping configuration, thereby defining a longitudinal axis;
    a pivot member positioned in closer proximity to the distal ends than the proximal ends that extends across each of the first and second arms and pivotally connects the arms together with the arms movable between an open orientation with the distal ends being spaced apart and a closed orientation with the distal ends being spaced together;
    a force mechanism attached in proximity to the proximal ends of the first and second arms, the force mechanism including:
        a first set of links positioned on a first lateral side of the first and second arms;
        a second set of links positioned on an opposing second lateral side of the first and second arms; and
        an elongated threaded element positioned between the first and second arms and between the first and second sets of links, the elongated threaded element including an threaded section that extends along a limited length of the element, a first unthreaded section that extends between the threaded section and a distal end of the element, and a second unthreaded section positioned on an opposing side of the threaded section from the first unthreaded section;

a connector with a threaded aperture that is positioned over the threaded section, the connector further including a first attachment with the first set of links and a second attachment with the second sets of links.

13. The surgical instrument of claim 12, further comprising a biasing member positioned on the first unthreaded section of the threaded element to bias the first connector towards the threaded section.

14. The surgical instrument of claim 12, wherein the first arm, the second arm, and the threaded element are aligned within a common plane.

15. The surgical instrument of claim 12, further comprising a second connector including an aperture positioned over the second unthreaded section sized for the threaded element to be rotatable within the aperture, the second connector positioned between and being attached to each of the first and second sets of links.

16. The surgical instrument of claim 12, further including a passage that extends longitudinally through the first arm from an inlet at the distal end, through the pivot member, and to an outlet along the arm on an opposite side of the pivot member from the inlet.

17. The surgical instrument of claim 12, wherein the passage includes an axis transverse to the longitudinal axis.

18. The surgical instrument of claim 12, wherein the threaded element includes a proximal end that extends proximally outward beyond the first and second set of links.

19. The surgical instrument of claim 12, wherein the cutting elements of the first and second arms are aligned such that one of the cutting elements in front of the other when the arms are in the closed orientation.

* * * * *